US006482448B2

(12) United States Patent
Tabor

(10) Patent No.: US 6,482,448 B2
(45) Date of Patent: *Nov. 19, 2002

(54) SOY FORMULATIONS AND THEIR USE FOR PROMOTING HEALTH

(76) Inventor: Aaron Tabor, 726 Morris Rd., Winston-Salem, NC (US) 27101

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,167

(22) Filed: Jul. 16, 1999

(65) Prior Publication Data

US 2002/0103223 A1 Aug. 1, 2002

Related U.S. Application Data

(60) Provisional application No. 60/092,985, filed on Jul. 16, 1998, and provisional application No. 60/105,797, filed on Oct. 27, 1998.

(51) Int. Cl.[7] .................. A61K 31/70; A61K 33/00; A23L 1/36

(52) U.S. Cl. .................. 424/757; 514/28; 514/27; 426/629

(58) Field of Search .................. 514/28, 27; 424/757; 426/629

(56) References Cited

U.S. PATENT DOCUMENTS

| | | | |
|---|---|---|---|
| 3,864,362 A | | 2/1975 | Feuer et al. |
| 5,424,311 A | | 6/1995 | Billhardt-Troughton et al. |
| 5,424,331 A | | 6/1995 | Shlyankevich |
| 5,498,631 A | | 3/1996 | Gorbach et al. |
| 5,506,211 A | | 4/1996 | Barnes et al. |
| 5,516,528 A | | 5/1996 | Hughes et al. |
| 5,523,087 A | | 6/1996 | Shlyankevich |
| 5,569,459 A | | 10/1996 | Shlyankevich |
| 5,654,011 A | | 8/1997 | Jackson et al. |
| 5,707,630 A | | 1/1998 | Morrow |
| 5,733,926 A | | 3/1998 | Gorbach |
| 5,776,906 A | | 7/1998 | Sekiya |
| 5,830,887 A | * | 11/1998 | Kelly .................. 514/182 |
| 5,855,892 A | * | 1/1999 | Potter et al. .............. 424/195.1 |
| 5,858,449 A | * | 1/1999 | Crank et al. .................. 426/656 |
| 5,942,539 A | | 8/1999 | Hughes, Jr. et al. |
| 5,952,374 A | | 9/1999 | Clarkson, Jr. et al. |
| 6,060,070 A | | 5/2000 | Gorbach |
| 6,083,526 A | | 7/2000 | Gorbach |

FOREIGN PATENT DOCUMENTS

WO  93/23069  11/1993

OTHER PUBLICATIONS

USDA–Iowa State University Database on the Isoflavone content of Foods, p. 10, 1999.*

Tsukamoto C., et al: "Factors Affecting Isoflavone Content in Soybean Seeds: Changes in Isoflavones, Saponins, and Composition of Fatty Acids at Different Temperatures During Seed Development," Journal of Agricultural and Food Chemistry, vol. 43, No. 5, 1995, pp. 1184–1192, XP002129349, Taishi Foods Co., Ltd., 68 Okinaka, Kawamorita, Sannohe–machi, Sannohe–gun, Aomori–ken 039–01, Japan, p. 1187; tables 3, 4.

Huei–Ju Wang et al: "Isoflavone Composition of American and Japanese Soybeans in Iowa: Effects of Variety, Crop Year, and Location," Journal of Agricultural and Food Chemistry, vol. 42, No. 8, 1994, pp. 1674–1677, XP002129350, Correspondence (Reprint) address, P.A. Murphy, Food Sci. & Human Nutr., Iowa State Univ., Ames, IA 50011, USA. Tel. (511) 294–1970, p. 1675, col. 1; tables 1, 2.

Wang H–J et al: "Isoflavone Content in Commercial Soybean Foods," Journal of Agricultural and Food Chemisty, US American Chemical Society, Washington, vol. 42, No. 8, Jan. 1, 1994, pp. 1666–1673, XP002035317, ISSN: 0021–8561 p. 1668, col. 1–2; table 4.

Helferich B.: "Dietary Estrogens: A Balance of Risks and Benefits," Food Technology, US Institute of Food Technologists, Chicago, vol. 50, No. 9, Sep. 1, 1996, p. 158, XP000626807, ISSN: 0015–6639, the whole document.

Wiseman, H: "Dietary Phytoestrogens: Disease Prevention Versus Potential Hazards," Nutrition and Food Science, 1997, XP000866478 Dep. of Nutr. & Dietetics, King's Coll., London W8 7AH, UK, the whole document.

Gooderham, MJ, et al.: "A Soy Protein Isolate Rich in Genistein and Daidzein and its Effects on Plasma Isoflavone Concentrations, Platelet Aggregation, Blood Lipids and Fatty Acid Composition of Plasma Phospholipid in Normal Men," Journal of Nutrition, vol. 7, No. 126, 1996, pp. 2000–2006, XP000866098, Correspondence (Reprint) Address, B. Holub, Dep. Of Human Biol. & Nutr. Sci., Univ. of Guelph, Guelph, Ont. NIG 2WI, Canada, p. 2003–p. 2005.

(List continued on next page.)

Primary Examiner—Rebecca Cook
(74) Attorney, Agent, or Firm—Kilpatrick Stockton LLP

(57) ABSTRACT

The present invention provides novel soy formulations comprising 3–23 milligrams of at least one isoflavone per gram of the formulation. The soy formulations may additionally comprise 0.4 to 1.2 grams of protein per gram of the formulation. In another aspect, the present invention provides novel soy formulations comprising diadzin, genistin and glycitin in a ratio of 3:1:2 to 3:4.5:1, preferably approximately 2:1:1 such that diadzin is a major isoflavone component. The present invention further provides dietary supplements and food products comprising a soy formulation of the present invention.

In another aspect the present invention provides pharmacological compositions comprising a soy formulation of the present invention. The pharmacological compositions may additionally comprise a medicinal composition.

Also disclosed are methods for promoting the health of an individual, preferably utilizing the soy formulations, dietary supplements, food products and/or pharmacological compositions of the present invention.

23 Claims, No Drawings

OTHER PUBLICATIONS

Cassidy, A., et al.: "Biological Effects of Isoflavones in Young Women: Importance of the Chemical Composition of Soybean Products." British Journal of Nutrition, vol. 74, No. 4, 1995, pp. 587–601, XP000866160, Dunn Clinical Nutr. Cent., Hills Rd., Cambridge CB2 2DH, UK, pp. 597–599.

Tham, Doris M., et al., "Clinical Review 97: Potential Health Benefits of Dietary Phytoestrogens: A Review of the Clinical, Epidemiological, and Mechanistic Evidence," Journal of Clinical Endocrinology and Metabolism, 1998, pp. 2223–2225, vol. 83, No. 7, Stanford Center for Research in Disease Prevention and the Department of Medicine, Stanford University Medical School, Stanford, CA.

Albertazzi, P., et al., "The Effect of Dietary Soy Supplementation on Hot Flushes," Obstetrics & Gynecology, Jan. 1998, pp. 6–11, vol. 91, No. 1, Menopause and Osteoporosis Center, University of Ferrara, Italy.

Knight, D.C., et al., "A Review of the Clinical Effects of Phytoestrogens," Obstetrics & Gynecology, May 1996, pp. 897–904, vol. 87 No. 5, Pt. 2, Royal Hospital for Women, New South Wales, Australia.

Washburn, S., et al., "Effect of Soy Protein Supplementation on Serum Lipoproteins, Blood Pressure, and Menopausal Symptons in Perimenopausal Women," Menopause, Spring 1999, pp. 7–13, vol. 6, No. 1, Department of Obstetrics and Gynecology, Wake Forest University School of Medicine, Winston, Salem, NC.

Anderson, J.W., et al., "Meta–Analysis of the Effects of Soy Protein Intake on Serum Lipids," New England Journal of Medicine, Aug. 3, 1995, pp. 276–282, vol. 333, No. 5, Metabolic Research Group, Veterans Affairs Medical Center, Lexington, KY.

Kapiotis, S., et al., "Genistein, the Dietary–Derived Angiogenesis Inhibitor, Prevents LDL Oxidation and Protects Endothelial Cells from Damage by Atherogenic LDL," Arterioscler Thromb Casc Biol, Nov. 1997, pp. 2868–2874, vol. 17, No. 11, Clinical Institute of Medical and Chemical Laboratory Diagnostics, University of Vienna, Austria.

American Journal of Clinical Nutrition, Dec. 1998, pp. 1390S–1393S, vol. 68, Suppl. 6, Comparative Medicine Clinical Research Center, Bowman Gray School of Medicine of Wake Forest University, Winston–Salem, NC.

Baum, J.A., et al., "Long–Term Intake of Soy Protein Improves Blood Lipid Profiles and Increases Mononuclear Cell Low–Density–Lipoprotein Receptor Messenger RNA in Hypercholesterolemic, Postmenopausal Women," American Journal of Clinical Nutrition, Sep. 1998, pp. 545–551, vol. 68, No. 3, Department of Food Science and Human Nutrition, University of Illinois at Urbana/Champaign.

Anderson, J.W., et al., "Effects of Soy Protein on Renal Function and Proteinuria in Patients with Type 2 Diabetes," American Journal of Clinical Nutrition, Dec. 1998, pp. 1347S–1353S, vol. 68, Suppl. 6, Metabolic Research Group, VA Medical Center and University of Kentucky, Lexington.

Ingram, D., et al., "Case–Control Study of Phyto–oestrogens and Breast Cancer," Lancet, Oct. 4, 1997, pp. 990–994, vol. 350, No. 9083, University Department of Surgery, Queen Elizabeth II Medical Centre, Perth, Western Australia.

Zheng, W., et al., "Urinary Excretion of Isoflavonoids and the Risk of Breast Cancer," Cancer Epidemiology Biomarkers Prev, Jan. 1999, pp. 35–40, vol. 8, No. 1, School of Public Health and Cancer Center, University of South Carolina, Columbia.

Xu, X., et al., "Effects of Soy Isoflavones on Estrogen and Phytoestrogen Metabolism in Premenopausal Women," Cancer Epidemiology Biomarkers Prev, Dec. 1998, pp. 1101–1108, vol. 7, No. 12, Department of Food Science and Nutrition, University of Minnesota, St. Paul.

New Texas Research Shows Soy Diets Lower Estrogen; 'Reducing Estrogen Reduces Breast Cell Proliferation', Apr. 15, 1999.

Shao, Z.M., et al., "Genistein Exerts Multiple Suppressive Effects on Human Breast Carcinoma Cells," Cancer Res, Nov. 1, 1998, pp. 4851–4857, vol. 58, No. 21, Department of Surgery, Cancer Hospital/Cancer Institute, Shanghai Medical University, People's Republic of China.

Constantinou, A.I., et al., "Genistein Inactivates bcl–2, Delays the G2/M Phase of the Cell Cycle, and Includes Apoptosis of Human Breast Adenocarcinoma MCF–7 Cells," Eur J Cancer, Nov. 1998, pp. 1927–1934, vol. 34, No. 12, Department of Surgical Oncology, College of Medicine, University of Illinois at Chicago.

Foth, D., et al., "Effects of Mammalian and Plant Estrogens on Mammary Glands and Uteri of Macaques," American Journal of Clinical Nutrition, Dec. 1998, pp. 1413S–1417S, vol. 68, Suppl. 6, Department of Obstetrics of Gynecology, Ernst–Moritz–Arndt University, Greifswald, Germany.

Goodman, M.T., et al., "Association of Soy and Fiber Consumption with the Risk of Endometrial Cancer," American Journal of Epidemiology, Aug. 15, 1997, pp. 294–306, vol. 146, No. 4, Epidemiology Program, Cancer Research Center of Hawaii, University of Hawaii, Honolulu.

Potter, S.M., "Soy Protein and Isoflavones: Their Effects on Blood Lipids and Bone Density in Postmenopausal Women," American Journal of Clinical Nutrition, Dec. 1998, pp. 1375S–1379S, vol. 68, Suppl. 6, Department of Food Science and Human Nutrition, University of Illinois at Urbana–Champaign.

Harrison, E., et al., "The Effect of Soybean Protein on Bone Loss in a Rat Model of Postmenopausal Osteoporosis," J. Nutr. Sci Vitaminol, Apr. 1998, pp. 257–268, vol. 44, No. 2, Department of Adult Health, Faculty of Medicine, University of the Ryukyus, Okinawa, Japan.

Ishimi, Y., et al., "Selective Effects of Genistein, a Soybean Isoflavone, on B–lymphopoiesis and Bone Loss Caused by Estrogen Deficiency," Endocrinology, Apr. 1999, pp. 1893–1900, vol. 140, No. 4, Department of Food Science, The National Institute of Health and Nutrition, Tokyo, Japan.

Geller, J., "Genistein Inhibits the Growth of Human–patient BPH and Prostate Cancer in Histoculture," Prostate, 1998, pp. 75–79, vol. 34, AntiCancer, Inc., San Diego, CA, Department of Surgery, University of California School of Medicine, San Diego, CA, Mercy Hospital and Medical Center, San Diego, CA and Scripps Clinic, La Jolla, CA.

Dalu, A., et al., "Genistein, a Component of Soy, Inhibits the Expression of the EGF and ErbB2/Neu Receptors in the Rat Dorsolateral Prostate," Prostate, Sep. 15, 1998, pp. 36–43, vol. 37, No. 1, Department of Pharmacology and Toxicology, University of Alabama at Birmingham.

Davis, J.N., et al., "Genistein–Induced Upregulation of p21 WAF1, Downregulation of Cyclin B, and Induction of Apoptosis in Prostate Cancer Cells," Nutr Cancer, 1998, pp. 123–131, vol. 32, No. 3, Department of Cancer Biology, Wayne State University School of Medicine, Harper Hospital, Detroit Medical Center, MI.

Onozawa, M., et al., "Effects of Soybean Isoflavones on Cell Growth and Apoptosis of the Human Prostatic Cancer Cell Line LNCaP," Jpn J Clin Oncol, Jun. 1998, pp. 360–363, vol. 28, No. 6, Cancer Prevention Division, National Cancer Center Research Institute, Tokyo, Japan.

Jacobsen, B.K., et al., "Does High Soy Milk Intake Reduce Prostate Cancer Incidence? The Adventist Health Study," Cancer Causes Control, Dec. 1998, pp. 553–557, vol. 9, No. 6, Institute of Community Medicine, University of Tromso, Norway.

Landstrom, M., et al., "Inhibitory Effects of Soy and Rye Diets on the Development of Dunning R3327 Prostate Adenocarcinoma in Rats," Prostate, Aug. 1, 1998, pp. 151–161, vol. 36, No. 3, Department of Pathology, University of Umea, Sweden.

Strom, S.S., et al., "Phytoestrogen Intake and Prostate Cancer: A Case–Control Study Using a New Database," Nutr Cancer, 1999, pp. 20–25, vol. 33, No. 1, Department of Epidemiology, University of Texas M.D. Anderson Cancer Center, Houston.

Theodorescu, D., et al., "Inhibition of Human Bladder Cancer Cell Motility by Genistein is Dependent on Epidermal Growth Factor Receptor but not p21ras Gene Expression," Int J Cancer, Dec. 9, 1998, pp. 775–782, vol. 78, No. 6, Department of Urology, University of Virginia Health Sciences Center, Charlottesville.

Zhou, J.R., et al., "Inhibition of Murine Bladder Tumorigenesis by Soy Isoflavones Via Alterations in the Cell Cycle, Apoptosis, and Angiogenesis," Cancer Res, Nov. 15, 1998, pp. 5231–5238, vol. 58, No. 22, Department of Surgery, Beth Israel–Deaconess Medical Center, Harvard Medical School, Boston, Massachusetts.

Thiagarajan, D.G., et al., "Prevention of Precancerous Colonic Lesions in Rats by Soy Flakes, Soy Flour, Genistein, and Calcium," Am J Clin Nutr, Dec. 1998, pp. 1394S–1399S, vol. 68 (Suppl. 6), Department of Food Science and Human Nutrition, Michigan State University, East Lansing.

Yu, J., et al., "Effects of Genistein nd Daidzein on Membrane Characteristics of HCT Cells," Nutr Cancer, 1999, pp. 100–104, vol. 33, No. 1, Department of Biological Sciences and Biotechnology, Tsinghua University, Beijing, People's Republic of China.

Reuters Health, Westport Newsroom 203 319–2700, "Soy Protein Appears to Reduce Colon Cancer Incidence," Sep. 3, 1999.

PRNewswire, Good Morning America' Cites Benefits of Soy Foods: Isoflavones Promote Health, Evidence Worldwide' Finds, Jul. 16, 1999, Foods for the Future, CO: American Broadcasting Company.

Bong Ryoul, Oh., et al., "Association of Benign Prostatic Hyperplasia with Male Pattern Baldness," Urology, Elsevier Science Inc. 1998, vol. 51, No. 5, pp. 744–748.

Morton, M.S., et al., "Lignans and Isoflavonoids in Plasma and Prostatic Fluid in Men: Samples from Portugal, Hong Kong, and the United Kingdom," Prostate, Wiley–Liss, Inc., 1997, vol. 32, pp. 122–128.

Evans, B.A.J., et al., "Inhibition of 5α–Reductase in Genital Skin Fibroblasts and Prostate Tissue by Dietary Lignans and Isoflavonoids," Journal of Endocrinology, Journal of Endocrinology Ltd., Great Britain, 1995, vol. 147, pp. 295–302.

Negri–Cesi, Paola, et al., "Presence of 5α–Reductase Isozymes and Aromatase in Human Prostate Cancer Cells and in Benign Prostate Hyperplastic Tissue," Prostate, Wiley–Liss, Inc., 1998, vol. 34, pp. 283–291.

Yip, Ian, et al., "Nutritional Approaches to the Prevention of Prostate Cancer Progression," Dietary Fats, Lipids, Hormones, and Tumorigenesis, Plenum Press, New York, 1996, pp. 173–181.

Mäkelä, S., et al., "Inhibition of 17β–Hydroxysteroid Oxidoreductase by Flavonoids in Breast and Prostate Cancer Cells," Inhibition of 17β–HSOR by Flavonoids, Society for Experimental Biology and Medicine, 1998, pp. 310–316.

Lock, Margaret, "Contested Meanings of the Menopause," The Lancet, vol. 337, May 25, 1991, pp. 1270–1272.

Lampe, Johanna W., et al., "Urinary Equol Excretion with a Soy Challenge: Influence of Habitual Diet,".

Murkies, Alice, et al., "Clinical Review 92 Phytoestrogens," Journal of Clinical Endocrinology and Metabolism, The Endocrine Society, 1998, vol. 83, No. 2, pp. 297–303.

Barnes, Stephen, "Evolutionof the Health Benefits of Soy Isoflavones," P.S.E.B.M, Society for Experimental Biology and Medicine, 1998, vol. 217, pp. 386–392.

Clarkson, Thomas, "The Potential of Soybean Phytoestrogens for Postmenopausal Hormone Replacement Therapy," P.S.E.B.M., Society for Experimental Biology and Medicine, 1998, vol. 217, pp. 365–368.

Davis, Susan, et al., "Phytoestrogens in Clinical Practice," Integrative Medicine, Elsevier Science Inc., 1998, vol. 1, No. 1, pp. 27–34.

"Soy Protein's Phytoestrogens May Serve as Alternative to Traditional Hormone Replacement Therapy," American Heart News (a publication of the American Heart Association) 70th Scientific Sessions 1997.

Knight, David, et al., "Phytoestrogens—a Short Review," Maturitas: Journal of the Climacteric & Postmenopause, Elsevier Science Ireland Ltd, 1995, vol. 22, pp. 167–175.

Anderson, John, et al., "Phytostrogens and Human Function," Nutrition Today, vol. 32, No. 6, Nov./Dec. 1997, pp. 232–239.

"Scientists Spotlight Phytoestrogens for Better Health," reprinted from Tufts University Diet & Nutrition Letter, Feb. 1995, pp. 3–6.

Clarkson, Thomas, "Can Soy Phytoestrogens Substitute for Traditional Hormone Replacement Therapy?" Menopausal Medicine, vol. 5, No. 3, Fall 1997, pp. 1–4.

Murkies, A.L., et al., "Dietary Flour Supplementation Decreases Post–Menopausal Hot Flushes: Effect of Soy and Wheat," Maturitas: Journal of the Climacteric & Postmenopause, Elsevier Science Ireland Ltd, 1995, vol. 21, pp. 189–195.

"AHA Conference: Key Ingredient In Soy is What Lowers Cholesterol Levels," webmaster@pslgroup.com, P/S/L Consulting Group Inc., 1998, pp. 1–2.

"AHA Conference: Soy Phytoestrogens Prevent Stroke as Much as Premarin," webmaster@pslgroup.com, P/S/L Consulting Group Inc, 1998, pp. 1–2.

Lamartiniere, Coral, et al., "Genistein Alters the Ontogeny of Mammary Gland Development and Protects Against Chemically–Induced Mammary Cancer in Rats," P.S.E.B.M, Society for Experimental Biology and Medicine, 1998, vol. 217, pp. 358–364.

Erdman, John, et al., "Soy and Bone Health," The Soy Connection, United Soybean Board, vol. 5, No. 2, Spring 1997, pp. 1–2.

Cassidy, Aedin, "Biological Effects of a Diet of Soy Protein Rich in Isoflavones on the Menstrual Cycle of Premenopausal Women," Am. J. Clin. Nutr., American Society for Clinical Nutrition, 1994, vol. 60, pp. 333–340.

* cited by examiner

SOY FORMULATIONS AND THEIR USE FOR PROMOTING HEALTH

STATEMENT OF RELATED APPLICATIONS

The present application claims priority from U.S. provisional patent application Ser. No. 60/092,985, filed Jul. 16, 1998 and U.S. provisional patent application Ser. No. 60/105,797, filed Oct. 27, 1998. The disclosure of each provisional application is hereby incorporated herein by reference.

FIELD OF THE INVENTION

The present invention relates to soy formulations, dietary supplements comprising the soy formulations and food products which include the soy formulations and/or the dietary supplements. The present invention also relates to pharmacological compositions comprising the soy formulation that may additionally comprise a medicinal composition. The present invention further relates to processes for producing soy formulations. In addition, the present invention relates to methods for promoting the health of an individual utilizing the soy formulations, dietary supplements, food products and/or pharmacological compositions of the present invention.

BACKGROUND

Soybeans include natural plant estrogens, known as phytoestrogens or isoflavones. These isoflavones are thought to bind to estrogen receptors and thus exert an estrogenic response. Medical studies have shown that isoflavones in soy protein have many beneficial interactions with a variety of human tissues, are safe, cause no significant side-effects, and are the primary reason for many health benefits. Research has discovered in Asian countries like Japan, where the traditional diet is high in soy protein, very few women complain about menopausal symptoms, for example only 9% of Japanese women complain about hot flashes. In addition, younger women have fewer menstrual periods per year, and occurrences of some cancers (breast and endometrial), heart disease, and other chronic diseases are very low. It has been reported that Japanese women consume up to 200 mg of isoflavones in their daily diet and have a lower incidence of perimenstrual and menopausal symptoms than women in other cultures consuming less daily dietary isoflavones. Previous studies using isoflavone dosages of 76 mg per day report a 45% reduction in hot flashes in women after 12 weeks.

In addition to providing isoflavones, soybeans provide a source of protein. It is believed that the benefits from soy come from the phytoestrogens (isoflavones) other compounds such as lignans and saponins, the soy protein itself and undoubtedly undiscovered compounds.

Several soy protein formulations are commercially available. Formulations produced exclusively from the whole soy bean generally include 1–5 milligrams isoflavone per gram of the formulation and may be up to 90% protein. Formulations produced exclusively from the heart (center) of the soy bean generally include 24–36 milligram isoflavone per gram of the formulation. Although tablets with concentrations of 100–750 milligram isoflavones per gram are available, formulations having concentrations greater than 36 mg isoflavones per gram of the formulation are chemically extracted and modified and therefore are not considered natural.

Dietary levels of 60 milligrams, in particular 120–200 milligrams of isoflavones are difficult to achieve utilizing currently available natural soy protein formulations. To achieve a dietary level of greater than 60 milligrams, and in particular 120–200 milligrams of isoflavones from soy formulations produced utilizing the whole soy bean could require ingesting greater than 60 grams, in particular up to 120–200 grams of soy protein. Intake of soy protein at this volume level tends to cause digestive side effects such as bloating and constipation. To achieve a dietary level of greater than 60 milligrams, preferably 120–200 milligrams, of isoflavones from soy formulations produced utilizing the heart of the soy bean may require ingesting only 3 to 8 grams of soy protein. However, with soy protein levels this low, the person ingesting the formulation would be receiving minimal benefits and nutritional value from soy protein itself.

Accordingly, it would be advantageous to have a natural soy formulation having a milligram isoflavone to gram of the formulation ratio falling between the ratios of natural soy formulations produced from the whole soybean and natural soy formulations produced from the heart of the soy bean.

It would also be advantageous to have dietary supplements that include the natural soy formulations. In particular, it would be advantageous to have dietary supplements which when ingested in reasonable amounts provide dietary isoflavone levels of greater than 60 milligrams, preferably greater than 120 milligrams, for example 120–200 milligrams or higher, e.g. greater than 200 milligrams. For certain applications it may be advantageous to have dietary supplements or soy formulations that provide dietary isoflavone levels as high as 1500–2200 milligrams, or greater.

Further, it would be advantageous to have food products that include the natural soy formulations and/or the natural dietary supplements. In particular, it would also be advantageous to have food products which when ingested in reasonable amounts provide dietary isoflavone levels of greater than 60 milligrams, preferably greater than 120 milligrams, for example 120–200 milligrams, or higher, e.g. greater than 200 milligrams, up to 400–900 milligrams or greater. For certain applications it may be advantageous to have food products, dietary supplements or soy formulations that provide dietary isoflavone levels as high as 1500–2200 milligrams, or greater.

These and other advantages are achieved by the present invention.

SUMMARY OF THE INVENTION

The present invention provides soy protein formulations (soy formulations), dietary supplements and food products (including medical foods) comprising the soy formulations and/or dietary supplements. The present invention also provides pharmaceutical compositions.

A soy formulation of the present invention includes a higher concentration of natural plant estrogens, referred to as isoflavones or phytoestrogens, per gram of the formulation, than currently available in a natural product. The soy formulation may further include protein, therefore providing a higher concentration of isoflavones per gram of the formulation, and per gram of protein in the formulation, than currently available in a natural product.

The isoflavone component of the soy formulation of the present invention may comprise naturally occurring isoflavones, including, but not limited to: diadzin, genistin, and glycitin. In another aspect, the present invention provides soy formulations having diadzin as a major isoflavone component.

A dietary supplement of the present invention comprises a soy formulation of the present invention. The dietary supplement may further comprise ingredients such as enzymes, a fiber source, vitamins and the like.

A food product of the present invention comprises a soy formulation of the present invention and/or a dietary supplement of the present invention. The food product may further comprise additional ingredients.

A pharmaceutical composition of the present invention comprises a soy formulation of the present invention in a pharmacologically effective amount. The compositions may additionally comprise prescription medicines. The combination may advantageously produce one or more of the following effects:

1) additive and/or synergistic benefits;
2) reduction of the side effects and/or adverse effects associated with use of the prescription medicine in the absence of the soy formulation; and/or
3) the ability to lower the dosage of the prescription medicine in comparison to the amount of prescription medicine needed in the absence of the soy formulation.

Further advantages and possible embodiments of a drug formulation of the present invention are discussed in detail below.

The soy formulations, dietary supplements, food products and/or pharmaceutical compositions of the present invention may advantageously be utilized in methods for promoting the health of an individual. The soy formulations, dietary supplements, food products and pharmaceutical compositions of the present invention may provide higher concentrations of isoflavones than currently available soy products in a readily digestible and absorbable form.

The soy formulations, dietary supplements, food products and pharmaceutical compositions of the present invention may also provide protein. The isoflavones and/or protein provided by the soy formulations, dietary supplements, food products and pharmaceutical compositions of the present invention may provide numerous health benefits to an individual. In particular, the soy formulations, dietary supplements, food products and pharmaceutical compositions of the present invention may be ingested in amounts that provide greater than 60 milligrams, and in certain embodiments greater than 200 milligrams, or greater than 1800 milligrams, and that may additionally provide greater than 20 grams of protein, without the unpleasant side effects individuals have experienced with prior products.

Further details and advantages of the present invention are provided in the following more detailed description.

DETAILED DESCRIPTION OF THE INVENTION

In one aspect, the present invention provides a soy formulation which includes a higher concentration of natural plant estrogens (referred to as isoflavones or phytoestrogens) per gram of protein than previously available. A soy formulation of the present invention comprises 3 to 23 milligrams of at least one isoflavone per gram of the formulation. Preferably a soy formulation of the present invention comprises 5 to 15 milligrams of at least one isoflavone per gram of the formulation, more preferably, 6–9 milligrams of at least one isoflavone per gram of the formulation.

In this aspect, the present invention provides a natural soy formulation comprising 3 to 23 milligrams of at least one isoflavone per gram of the formulation. In embodiments of the present invention the natural soy formulation may comprise 5 to 15 milligrams of at least one isoflavone per gram of the formulation, or 6 to 9 milligrams of at least one isoflavone per gram of the formulation.

The isoflavone component of the soy formulation of the present invention preferably comprises naturally occurring isoflavones, including, but not limited to: diadzin, genistin, and/or glycitin.

In another aspect, the present invention provides a soy formulation comprising diadzin, genistin and glycitin and having a diadzin to genistin to glycitin ratio of between 3:1:2 and 3:4.5:1. In other words, in this aspect the soy formulation comprises 3 parts diadzin; 1 to 4.5 parts genistin; and 1 to 2 parts glycitin. Preferably a soy formulation of the present invention has a ratio of diadzin to genistin to glycitin of near or approximately 2:1:1, respectively, such that diadzin is the major isoflavone component.

Although the isoflavones discussed herein are discussed with reference to their glycone forms, the present invention may utilize aglycone forms of isoflavones which may be digested and/or absorbed more easily by an individual. The aglycone form refers to glycone after cleavage of the glucose subgroup.

In a further aspect, the soy formulations of the present invention comprise 0.4 to 1.2 grams, preferably 0.4 to 0.9 grams, more preferably 0.6 to 0.8 grams of protein per gram of the formulation. Thus, an embodiment of a soy formulation of the present invention comprises:

3 to 23 milligrams, preferably 5 to 15 milligrams, more preferably, 6–9 milligrams of at least one isoflavone; and 0.4 to 1.2 grams, preferably 0.4 to 0.9 grams, more preferably 0.6 to 0.8 grams protein; per gram of the formulation.

The soy formulation may further include a plurality of isoflavones, including diadzin, genistin and glycitin. In an embodiment the soy formulation has a diadzin to genistin to glycitin ratio of between 3:1:2 and 3:4.5:1. More preferably the soy formulation may have a ratio of diadzin to genistin to glycitin of near or approximately 2:1:1, respectively, such that diadzin is the major isoflavone component.

In yet a further aspect, the present invention provides a soy formulation produced by combining a first portion of higher isoflavone concentration soy product produced from the heart of the soy bean and a second portion of lower isoflavone concentration soy product produced from the whole soy bean to achieve a soy formulation comprising 3 to 23 milligrams of at least one isoflavone per gram of the formulation, preferably 5 to 15 milligrams of at least one isoflavone per gram of the formulation, more preferably, 6–9 milligrams of at least one isoflavone per gram of the formulation. The isoflavone(s) may comprise diadzin, genistin and glycitin. The soy formulation thus obtained may further comprise 0.4 to 1.2 grams, preferably 0.4 to 0.9 grams, more preferably 0.6 to 0.8 grams protein; per gram of the formulation. It is further preferred that the soy formulation include the diadzin—genistin—glycitin ratios discussed above.

A soy formulation of the present invention may take many forms. For example, the soy formulations of the present invention may be in powder form. Alternatively, the soy formulations may be in tablet or liquid form. In addition, the soy formulations of the present invention may be included within a dietary supplement, or within food items, such as nutrition bars, liquid drinks, cereals etc., in a food product of the present invention.

The soy formulations of the present invention may be utilized in dietary supplements. In one aspect, a dietary supplement of the present invention comprises a soy formulation of the present invention. The dietary supplement may comprise a soy formulation having one or more of the features described above. The amount of soy formulation utilized in a dietary supplement of the present invention will depend on the level of isoflavones desired per serving or dose of the dietary supplement. As further explained below, it is generally desirable for the dietary supplement to provide greater than 60 milligrams of at least one isoflavone per serving or dose. Thus, for example, a serving of a dietary supplement of the present invention could comprise 10 grams of a soy formulation of the present invention comprising 7 milligrams of at least one isoflavone per gram of the formulation, to provide 70 milligrams of isoflavones. To achieve higher levels of isoflavones, the dietary supplement could include additional amounts of a soy formulation and/or a soy formulation having a higher level of isoflavones per gram.

Thus an embodiment of a dietary supplement comprises: a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams of at least one isoflavone per serving.

In another embodiment, a dietary supplement of the present invention comprises: a soy formulation comprising 3 to 23 milligrams, preferably 5 to 15 milligrams, more preferably, 6–9 milligrams of at least one isoflavone per gram of the formulation; and 0.4 to 1.2 grams, preferably 0.4 to 0.9 grams, more preferably 0.6 to 0.8 grams protein; per gram of the formulation; wherein the amount of the soy formulation is sufficient to provide greater than 60 milligrams of at least one isoflavone per serving.

In a further embodiment, a dietary supplement of the present invention comprises: a soy formulation produced by combining a first portion of higher isoflavone concentration soy product produced from the heart of the soy bean and a second portion of lower isoflavone concentration soy product produced from the whole soy bean to achieve a soy formulation comprising 3 to 23 milligrams of at least one isoflavone per gram of the formulation, preferably 5 to 15 milligrams of at least one isoflavone per gram of the formulation, more preferably, 6–9 milligrams of at least one isoflavone per gram of the formulation wherein the amount of the soy formulation in the dietary supplement is sufficient to provide greater than 60 milligrams of at least one isoflavone per serving.

The isoflavone components and/or their ratios include those discussed above with reference to the soy formulations of the present invention. In particular embodiments of a dietary supplement of the present invention the amount of soy formulation utilized may be an amount sufficient to provide well above 60 milligrams of at least one isoflavone per serving. In particular embodiments of a dietary supplement the amount of soy formulation utilized may be an amount sufficient to provide 120–200 milligrams of at least one isoflavone per serving; greater than 200 milligrams of at least one isoflavone per serving; 400 to 900 milligrams of at least one isoflavone per serving; greater than 1800 milligrams of at least one isoflavone per serving; or 1800 to 2200 milligrams of at least one isoflavone per serving.

In a still further embodiment, a dietary supplement of the present invention comprises: a soy formulation comprising diadzin, genistin and glycitin and having a diadzin to genistin to glycitin ratio of between 3:1:2 and 3:4.5:1. Preferably the soy formulation has a ratio of diadzin to genistin to glycitin of near or approximately 2:1:1, respectively, such that diadzin is the major isoflavone component. In this embodiment, the dietary supplement may provide any milligram level of at least one isoflavone per serving, thus differing amounts of the soy formulation may be utilized in the dietary supplement. In specific embodiments according to this aspect of a dietary supplement of the present invention the amount of soy formulation utilized is sufficient to provide greater than 60 milligrams of at least one isoflavone per serving. In particular embodiments of this dietary supplement the amount of soy formulation utilized may be an amount sufficient to provide 120–200 milligrams of at least one isoflavone per serving; greater than 200 milligrams of at least one isoflavone per serving; 400 to 900 milligrams of at least one isoflavone per serving; greater than 1800 milligrams of at least one isoflavone per serving; or 1800 to 2200 milligrams of at least one isoflavone per serving.

In another aspect, a dietary supplement of the present invention comprises a soy formulation of the present invention and is further characterized by comprising: 40 to 90%, preferably 70 to 90%, by weight, protein; 1 to 10%, preferably 1 to 5%, by weight, fat; and 1 to 59%, preferably 1 to 25%, by weight, carbohydrate. The analysis of protein, carbohydrate and fat levels may be accomplished utilizing conventional techniques.

In another aspect, a dietary supplement of the present invention further comprises one or more of the following ingredients: digestive enzymes, fibers, sweeteners, preservatives, vitamins, minerals and the like, including but not limited to calcium phosphate, soy lecithin, salt, potassium, chloride, artificial and/or natural flavorings, carragenenen, carboxymethylcellulose, xantham gum, or milk solids. Suitable digestive enzymes include, but are not limited to: alpha galactosidase. Suitable fiber sources include, but are not limited to: psyllium. Suitable sweeteners include, but are not limited to, natural sweeteners, including sucrose, dextrose, fructose and the like; artificial sweeteners including sucralose (Splenda™), aspartame, saccharin and SinetK™ (acesulfurame K) and the like; and plant derived sweeteners including stevia. The amounts of the one or more additional ingredients are such that the dietary supplement maintains the protein, carbohydrate and fat ratios set forth above.

A dietary supplement of the present invention may be in any digestible form, including a powder, a tablet or in liquid form. A dietary supplement of the present invention may also be agglomerated and/or otherwise treated to improve solubility, digestibility or other aspects of the dietary supplement.

As will be understood by those of ordinary skill in the art, a dietary supplement of the present invention may also include ingredients similar to those set forth below with respect to a food product of the present invention.

In a further aspect the present invention provides a digestible food product which includes greater than 60 milligrams of at least one isoflavone per serving. In particular embodiments of this dietary supplement the amount of soy formulation utilized may be an amount sufficient to provide 120–200 milligrams of at least one isoflavone per serving; greater than 200 milligrams of at least one isoflavone per serving; 400 to 900 milligrams of at least one isoflavone per serving; greater than 1800 milligrams of at least one isoflavone per serving; or 1800 to 2200 milligrams of at least one isoflavone per serving.

In one aspect, a food product of the present invention comprises a soy formulation of the present invention. The dietary supplement may comprise a soy formulation having one or more of the features described above. The amount of soy formulation utilized in a food product of the present invention will depend on the level of isoflavones desired per serving of the food product. As further explained below, it is generally desirable for the food product to provide greater than 60 milligrams of at least one isoflavone per serving. Thus, for example, a serving of a food product of the present invention could comprise 8 grams of a soy formulation of the present invention comprising 9 milligrams of at least one isoflavone per gram of the formulation, to provide 72 milligrams of isoflavones. To achieve higher levels of isoflavones, the food product could include additional amounts of a soy formulation and/or a soy formulation having a higher level of isoflavones per gram.

Thus an embodiment of a food product comprises: a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams of at least one isoflavone per serving.

In another embodiment, a food product of the present invention comprises: a soy formulation comprising 3 to 23 milligrams, preferably 5 to 15 milligrams, more preferably, 6–9 milligrams of at least one isoflavone per gram of the formulation; and 0.4 to 1.2 grams, preferably 0.4 to 0.9 grams, more preferably 0.6 to 0.8 grams protein; per gram of the formulation; wherein the amount of the soy formulation is sufficient to provide greater than 60 milligrams of at least one isoflavone per serving.

In a further embodiment, a food product of the present invention comprises: a soy formulation produced by combining a first portion of higher isoflavone concentration soy product produced from the heart of the soy bean and a second portion of lower isoflavone concentration soy product produced from the whole soy bean to achieve a soy formulation comprising 3 to 23 milligrams of at least one isoflavone per gram of the formulation, preferably 5 to 15 milligrams of at least one isoflavone per gram of the formulation, more preferably, 6–9 milligrams of at least one isoflavone per gram of the formulation wherein the amount of the soy formulation in the food product is sufficient to provide greater than 60 milligrams of at least one isoflavone per serving.

The isoflavone components and/or their ratios include those discussed above with reference to the soy formulations of the present invention. In particular embodiments of a food product of the present invention the amount of soy formulation utilized may be an amount sufficient to provide well above 60 milligrams of at least one isoflavone per serving. In particular embodiments of a food product the amount of soy formulation utilized may be an amount sufficient to provide 120–200 milligrams of at least one isoflavone per serving; greater than 200 milligrams of at least one isoflavone per serving; 400 to 900 milligrams of at least one isoflavone per serving; greater than 1800 milligrams of at least one isoflavone per serving; or 1800 to 2200 milligrams of at least one isoflavone per serving.

In a still further embodiment, a food product of the present invention comprises: a soy formulation comprising diadzin, genistin and glycitin and having a diadzin to genistin to glycitin ratio of between 3:1:2 and 3:4.5:1. Preferably the soy formulation has a ratio of diadzin to genistin to glycitin of near or approximately 2:1:1, respectively, such that diadzin is the major isoflavone component. In this embodiment, the food product may provide any milligram level of at least one isoflavone per serving, thus differing amounts of the soy formulation may be utilized in the food product. In specific embodiments according to this aspect of a food product of the present invention the amount of soy formulation utilized is sufficient to provide greater than 60 milligrams of at least one isoflavone per serving. In particular embodiments of this food product the amount of soy formulation utilized may be an amount sufficient to provide 120–200 milligrams of at least one isoflavone per serving; greater than 200 milligrams of at least one isoflavone per serving; 400 to 900 milligrams of at least one isoflavone per serving; greater than 1800 milligrams of at least one isoflavone per serving; or 1800 to 2200 milligrams of at least one isoflavone per serving.

In another aspect a food product of the present invention may preferably comprise:

20 to 40%, by weight, protein, preferably provided by a soy formulation of the present invention;

10 to 80%, by weight carbohydrate; and 1 to 10%, by weight fat.

The food product may further comprise additional components including preservatives, flavorings, vitamins, minerals and the like, including but not limited to calcium phosphate, soy lecithin, salt, potassium, chloride, artificial and natural flavors, carragenenan, carboxymethylcellulose, xantham gum, water or milk. Among the carbohydrates suitable for use in the present invention are included fructose, glucose, dextrose, maltodextrin and corn syrup solids.

A food product of the present invention may also be produced in a lower calorie form by substituting an artificial sweetener for all or a portion of the sugars. Suitable artificial sweeteners include sucralose (Splenda™), aspartame, saccharin and SinetK™ (acesulfurame K). Plant derived sweeteners such as stevia are also suitable.

A food product of the present invention may take many forms, including a powder for dispersing in a liquid, a tablet, a bar, liquid drinks, a cereal etc. By way of example, a powdered food product of the present invention may comprise:

30 to 32%, by weight a soy formulation of the present invention;

55 to 57%, by weight carbohydrate;

3 to 5%, by weight fat;

0.2 to 1%, by weight calcium;

0.2 to 1%, by weight phosphorous;

0.1 to 0.7%, by weight sodium;

0.2 to 1%, by weight potassium; and include ingredients such as fructose, sugar, cocoa, calcium phosphate, maltodextrin, soy lecithin, salt, potassium chloride, artificial flavor, carrageenan, carboxymethyl cellulose and xanthan gum, wherein the food product provides greater than 60 milligrams, preferably 120–200 milligrams of at least one isoflavone per serving, preferably a plurality of isoflavones in the ratios discussed above.

A food product of the present invention may further include vitamins and minerals in an amount of up to 100% or more of the recommended daily allowance for each vitamin. In a preferred embodiment, a food product of the present invention may include 20–40% of the recommended daily allowance of most minerals.

In a further aspect, the present invention provides a pharmacological composition comprising a soy formulation of the present invention. The amount of soy formulation utilized in a pharmacological composition of the present invention will depend on the level of isoflavones desired per dose of the pharmacological composition. As further explained below, it is generally desirable for the pharmacological composition to provide greater than 60 milligrams, preferably greater than 200 milligrams, more preferably greater than 1800 milligrams, of at least one isoflavone per dose. Thus, for example, a serving of a pharmacological composition of the present invention could comprise 9 grams of a soy formulation of the present invention comprising 7 milligrams of at least one isoflavone per gram of the formulation, to provide 63 milligrams of isoflavones. To achieve higher levels of isoflavones, the pharmacological composition could include additional amounts of a soy formulation and/or a soy formulation having a higher level of isoflavones per gram.

Thus an embodiment of a pharmacological composition comprises: a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose.

In another embodiment, a pharmacological composition of the present invention comprises: a soy formulation comprising 3 to 23 milligrams, preferably 5 to 15 milligrams, more preferably, 6–9 milligrams of at least one isoflavone per gram of the formulation; and 0.4 to 1.2 grams, preferably 0.4 to 0.9 grams, more preferably 0.6 to 0.8 grams protein; per gram of the formulation; wherein the amount of the soy formulation is sufficient to provide greater than 60 milligrams, preferably greater than 200 milligrams, more preferably greater than 1800 milligrams, of at least one isoflavone per dose.

In a further embodiment, a pharmacological composition of the present invention comprises: a soy formulation produced by combining a first portion of higher isoflavone concentration soy product produced from the heart of the soy bean and a second portion of lower isoflavone concentration soy product produced from the whole soy bean to achieve a soy formulation comprising 3 to 23 milligrams of at least one isoflavone per gram of the formulation, preferably 5 to 15 milligrams of at least one isoflavone per gram of the formulation, more preferably, 6–9 milligrams of at least one isoflavone per gram of the formulation wherein the amount of the soy formulation in the pharmacological composition is sufficient to provide greater than 60 milligrams, preferably greater than 200 milligrams, more preferably greater than 1800 milligrams, of at least one isoflavone per dose.

The isoflavone components and/or their ratios include those discussed above with reference to the soy formulations of the present invention. In particular embodiments of a pharmacological composition of the present invention the amount of soy formulation utilized may be an amount sufficient to provide well above 60 milligrams of at least one isoflavone per dose. In particular embodiments of a pharmacological composition the amount of soy formulation utilized may be an amount sufficient to provide 120–200 milligrams of at least one isoflavone per dose; greater than 200 milligrams of at least one isoflavone per dose; 400 to 900 milligrams of at least one isoflavone per dose; greater than 1800 milligrams of at least one isoflavone per dose; or 1800 to 2200 milligrams of at least one isoflavone per dose.

In a still further embodiment, a pharmacological composition of the present invention comprises: a soy formulation comprising diadzin, genistin and glycitin and having a diadzin to genistin to glycitin ratio of between 3:1:2 and 3:4.5:1. Preferably the soy formulation has a ratio of diadzin to genistin to glycitin of near or approximately 2:1:1, respectively, such that diadzin is the major isoflavone component. In this embodiment, the pharmacological composition may provide any milligram level of at least one isoflavone per dose, thus differing amounts of the soy formulation may be utilized in the pharmacological composition. In specific embodiments according to this aspect of a pharmacological composition of the present invention the amount of soy formulation utilized is sufficient to provide greater than 60 milligrams, preferably greater than 200 milligrams, more preferably greater than 1800 milligrams, of at least one isoflavone per dose. In particular embodiments of this pharmacological composition the amount of soy formulation utilized may be an amount sufficient to provide 120–200 milligrams of at least one isoflavone per dose; greater than 200 milligrams of at least one isoflavone per dose; 400 to 900 milligrams of at least one isoflavone per dose; greater than 1800 milligrams of at least one isoflavone per dose; or 1800 to 2200 milligrams of at least one isoflavone per dose.

As discussed above, and in detail below, a particular advantageous feature of the present invention is that in another aspect the present invention provides a pharmacological composition comprising a soy formulation of the present invention and further comprising a medicinal composition. Suitable medicinal compositions include, but are not limited to the medicinal compositions, drugs and/or prescription drugs utilized in estrogen replacement therapy; hormone replacement therapy; cholesterol lowering therapy; bone strengthening therapy; endometrial therapy; cancer therapy, including chemotherapy; alzeheimer's therapy; ulcer therapy; prostrate therapy; skin therapy; renal therapy; blood therapy; lymphatic therapy; lung therapy; nervous system therapy; diabetes therapy; eye therapy and the like. These medicinal compositions include, but are not limited to, Premarin; Fosamax; Raloxifene; Tamoxifen; SERM's (selective estrogen receptor modulators) and other drugs known to those of ordinary skill in the art.

The amount of the medicinal composition utilized in this embodiment of a pharmacological composition of the present invention is an amount sufficient to achieve the desired therapeutic effect while minimizing side or adverse effects. In general the amount of the medicinal composition utilized in a pharmacological composition of the present invention will be the same or less than the amount utilized in conventional therapy in the absence of the soy formulation of the present invention.

An advantage of a pharmacological composition of the present invention comprising a soy formulation of the present invention and a medicinal composition is that the combination may have synergistic effects. Therefore it may be possible to use a lesser amount of the medicinal composition in a pharmacological composition of the present invention than the amount traditionally utilized in the absence of a soy formulation of the present invention, while achieving substantially the same desired therapeutic effects. This feature also may provide an additional advantage of reducing side or adverse effects caused by the medicinal composition due to the lower amount of the medicinal composition utilized.

Further details, and specific examples of possible uses of pharmacological compositions of the present invention that comprise a soy formulation of the present invention and a medicinal composition are set forth below with reference to the methods of the present invention.

Thus, an embodiment of a pharmacological composition comprises: a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

In another embodiment, a pharmacological composition of the present invention comprises: a soy formulation comprising 3 to 23 milligrams, preferably 5 to 15 milligrams, more preferably, 6–9 milligrams of at least one isoflavone per gram of the formulation; 0.4 to 1.2 grams, preferably 0.4 to 0.9 grams, more preferably 0.6 to 0.8 grams protein; per gram of the formulation; and a medicinal composition wherein the amount of the soy formulation is sufficient to provide greater than 60 milligrams, preferably greater than 200 milligrams, more preferably greater than 1800 milligrams, of at least one isoflavone per dose and wherein the amount of the medicinal composition is sufficient to achieve a desired therapeutic effect.

In a further embodiment, a pharmacological composition of the present invention comprises: a soy formulation produced by combining a first portion of higher isoflavone concentration soy product produced from the heart of the soy bean and a second portion of lower isoflavone concentration soy product produced from the whole soy bean to achieve a soy formulation comprising 3 to 23 milligrams of at least one isoflavone per gram of the formulation, preferably 5 to 15 milligrams of at least one isoflavone per gram of the formulation, more preferably, 6–9 milligrams of at least one isoflavone per gram of the formulation wherein the amount of the soy formulation in the pharmacological composition is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

The isoflavone components and/or their ratios include those discussed above with reference to the soy formulations of the present invention. In particular embodiments of a pharmacological composition of the present invention the amount of soy formulation utilized may be an amount sufficient to provide well above 60 milligrams of at least one isoflavone per dose. In particular embodiments of a pharmacological composition the amount of soy formulation utilized may be an amount sufficient to provide 120–200 milligrams of at least one isoflavone per dose; greater than 200 milligrams of at least one isoflavone per dose; 400 to 900 milligrams of at least one isoflavone per dose; greater than 1800 milligrams of at least one isoflavone per dose; or 1800 to 2200 milligrams of at least one isoflavone per dose.

In a still further embodiment, a pharmacological composition of the present invention comprises: a soy formulation comprising diadzin, genistin and glycitin and having a diadzin to genistin to glycitin ratio of between 3:1:2 and 3:4.5:1; and a medicinal composition wherein the amount of the medicinal composition is sufficient to achieve a desired therapeutic effect. Preferably the soy formulation has a ratio of diadzin to genistin to glycitin of near or approximately 2:1:1, respectively, such that diadzin is the major isoflavone component. In this embodiment, the pharmacological composition may provide any milligram level of at least one isoflavone per dose, thus differing amounts of the soy formulation may be utilized in the pharmacological composition. In specific embodiments according to this aspect of a pharmacological composition of the present invention the amount of soy formulation utilized is sufficient to provide greater than 60 milligrams, preferably greater than 200 milligrams, more preferably greater than 1800 milligrams, of at least one isoflavone per dose. In particular embodiments of this pharmacological composition the amount of soy formulation utilized may be an amount sufficient to provide 120–200 milligrams of at least one isoflavone per dose; greater than 200 milligrams of at least one isoflavone per dose; 400 to 900 milligrams of at least one isoflavone per dose; greater than 1800 milligrams of at least one isoflavone per dose; or 1800 to 2200 milligrams of at least one isoflavone per dose.

Embodiments of a pharmacological composition of the present invention may further comprise a biologically compatible inert carrier composition comprising one or more of the following ingredients: a gel composition; a cellulose composition; a starch; a glycol composition; hydroxypropyl methylcellulose; microcrystalline cellulose; polyethylene glycol; and/or sodium lauryl sulfate. Other ingredients known in the art may also be utilized in the carrier composition.

Among the advantages of the soy formulations, dietary supplements, food products and pharmacological compositions of the present invention are that the soy formulations, dietary supplements, food products and pharmacological compositions may be utilized in the methods of the present invention to promote the health of an individual. In addition, the soy formulations, dietary supplements and food products provide a dietary means for providing beneficial amounts of an isoflavone, or a plurality of isoflavones, and protein to an individual, without requiring the individual ingests unpalatable or difficult to digest amounts of protein.

In addition to the soy formulations, dietary supplements, food products and pharmacological compositions discussed above, the present invention provides methods for promoting the health of an individual. A method of the present invention for promoting the health of an individual comprises having the individual ingest greater than 60 milligrams, preferably greater than 120 milligrams, more preferably 120–200 milligrams of at least one isoflavone per day. Embodiments of a method of the present invention may further comprise having the individual ingest greater than 200 milligrams of at least one isoflavone per day.

Preferably the individual will ingest the isoflavones by ingesting a soy formulation of the present invention, by ingesting a dietary supplement of the present invention, by ingesting a food product of the present invention, or by ingesting a pharmacological composition of the present invention. Thus, it is preferred that in a method of the present invention an individual ingests a soy formulation, a dietary supplement, food product and/or pharmacological composition including a soy formulation, comprising 3 to 23 milligrams of at least one isoflavone per gram of the formulation, more preferably 5 to 15 milligrams of at least one isoflavone per gram of the formulation, even more preferably, 6–9 milligrams of at least one isoflavone per gram of the formulation. The soy formulation utilized in a method of the present invention may further comprise 0.4 to 1.2 grams, preferably 0.4 to 0.9 grams, more preferably 0.6 to 0.8 grams protein; per gram of the formulation. The isoflavone(s) may comprise diadzin, genistin and/or glycitin. It is also preferred that in a method of the present invention an individual ingest the isoflavones in a diadzin to genistin to glycitin ratio of between 3:1:2 and 3:4.5:1, preferably a ratio of diadzin to genistin to glycitin of near or approximately 2:1:1, respectively, such that diadzin is the major isoflavone component.

The present invention also provides methods for enhancing health which include digesting a soy formulation of the present invention, and/or dietary supplements and/or food items and/or pharmacological compositions which include a soy formulation of the present invention.

A method of the present invention may be utilized to promote the health of an individual by reducing menopausal like symptoms, including hot flashes, pains and the like being experienced by the individual, for example as the result of a hysterectomy, breast cancer or a recent pregnancy. A method of the present invention may be utilized to promote the health of an individual by providing a dietary means of achieving the effects achieved by estrogen therapies.

Methods of the present invention may also be utilized to promote the health of an individual by reducing hot flashes, vaginal itching/dryness, irritability, mood swings, insomnia, night sweats, nervousness, headaches, and painful intercourse; soothing menstrual problems like cramping, bloating, irritability, and weight gain and to increase the time between menstrual periods (i.e., fewer periods per year); decreasing fatigue by boosting energy levels and mood; maintaining healthy breast tissue, endometrial tissue, and other tissues; preserving a strong and healthy skeletal system (bones and joints); and helping support a healthy heart, cardiovascular system, and cholesterol levels. Methods of the present invention may further be utilized to promote the health of an individual by minimizing the effects of Alzheimer's type dementia, age-related loss of cognitive function, and alcoholism. Other potential uses of the methods of the present invention include: birth control (at higher doses); hormone replacement therapy in combination with mammalian estrogens; breast cancer preventative; prostate cancer preventative; prevention and/or treatment of headaches and migraine headaches; prevention and/or treatment of acne and other skin conditions; improvement of sexual function; lessening effects of chronic fatigue syndrome; and weight loss.

As noted above, and in further detail below, methods of the present invention may be utilized to produce health benefits in an individual by alleviating or minimizing symptoms of the following conditions and/or providing health benefits in the following areas:

MENOPAUSE/PMS

Menopause symptoms like hot flushes, vaginal itching/dryness, irritability, mood swings, insomnia, night sweats.

Menopause-like symptoms.

Post-partum hot flushes.

Surgically-induced menopause symptoms (ie. oophorectomy).

PMS symptoms.

Normal menstrual complaints like cramping, bloating, irritability, and weight gain.

Abnormal vaginal bleeding of any cause.

Endometriosis, fibroids or other diseases where blocking estrogen could be beneficial.

In a particular embodiment of a method of the present invention for minimizing or alleviating symptoms of menopause/pms, the method comprises having an individual ingest a pharmacological composition of the present invention wherein the pharmacological composition comprises a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

A preferred medicinal composition for this embodiment is a medicinal composition for estrogen replacement therapy or hormone replacement therapy (estrogen+progestins). Premarin is an example of a medicinal composition for this embodiment of the method of the present invention The combination of a soy formulation of the present invention and a medicinal composition for hormone replacement therapy and/or estrogen replacement therapy may provide one or more of the following advantages:

1) an additive benefit to heart and bone tissues while reducing menopausal symptoms;

2) reduced breast and endometrial proliferation; or 3) a reduction in the amount of medicinal composition needed to achieve a therapeutic effect, for example less Premarin, resulting in lower cost to a patient and less risk.

HEART/CARDIOVASCULAR RELATED CONDITIONS

Lowering total cholesterol, LDL cholesterol, triglycerides and increasing HDL cholesterol or other favorable improvement in lipid profiles.

Lowering of blood pressure.

Prevention of myocardial infarction.

Prevention of second myocardial infarction.

Prevention or delaying restenosis of coronary bypass grafts or any other vascular grafts.

Prevention of stroke.

Improvement of cardiac stroke volume.

In a particular embodiment of a method of the present invention for benefiting heart/cardiovascular related conditions the method comprises having an individual ingest a pharmacological composition of the present invention wherein the pharmacological composition comprises a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

A preferred medicinal composition for this embodiment is Lipitor or another cholesterol lowering medication. The combination of a soy formulation of the present invention and a medicinal composition for cholesterol lowering may provide one or more of the following advantages:

1) an additive benefit to heart and bone tissues while generating a better lipid profile;

2) a reduction in the amount of medicinal composition needed to achieve a therapeutic effect, for example less Lipitor, resulting in lower cost to a patient and less risk of liver abnormalities caused by Lipitor.

BONE/SKELETAL SYSTEM CONDITIONS

Osteoporosis.

Hip fracture.

Quicker recovery after hip fracture surgery.

Disorders of the joints or cartilage.

Stimulation of growth and reduction of inflammation of connective tissue/joints.

In a particular embodiment of a method of the present invention for minimizing or alleviating symptoms of menopause/pms, the method comprises having an individual ingest a pharmacological composition of the present invention wherein the pharmacological composition comprises a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

A preferred medicinal composition for this embodiment is a medicinal composition for strengthening bones, estrogen replacement therapy or hormone replacement therapy (estrogen+progestins). Fosamax, Raloxifene and Premarin is an example of a medicinal composition for this embodiment of the method of the present invention. The combination of a soy formulation of the present invention and a medicinal composition may provide one or more of the following advantages:

1) an additive benefit to heart and bone tissues while reducing menopausal symptoms;
2) reduced breast and endometrial proliferation; or
3) a reduction in the amount of medicinal composition needed to achieve a therapeutic effect, for example less Premarin, resulting in lower cost to a patient and less risk.

BREAST/PROSTRATE RELATED CONDITIONS

Prevention and treatment of any abnormal breast tissue including, but not limited to, fibrocystic disease, ductal hyperplasia, ductal carcinoma in situ (DCIS), locally confined breast cancer or metastatic breast cancer.

Hot flushes and other menopause-like symptoms caused by breast cancer treatment or preventative treatment (eg. hot flashes caused by use of tamoxifen).

Improved quality/extension of life after diagnosis of breast tumor.

Early childhood treatment with isoflavones for prevention of breast cancer/prostate cancer later in life.

Reduces growth rate of cancerous tissue/cells.

Extension of life span after breast/prostate cancer.

In a particular embodiment of a method of the present invention for minimizing or alleviating symptoms of breast/prostrate related conditions, the method comprises having an individual ingest a pharmacological composition of the present invention wherein the pharmacological composition comprises a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

A preferred medicinal composition for this embodiment is a medicinal composition for estrogen replacement therapy or hormone replacement therapy (estrogen+progestins). Premarin is an example of a medicinal composition for this embodiment of the method of the present invention Other medicinal compositions include tamoxifen, raloxifene or SERM's. The combination of a soy formulation of the present invention and a medicinal composition may provide one or more of the following advantages:

1) an additive benefit to heart and bone tissues while having a preventive effect for breast cancer;
2) reduced breast and endometrial proliferation; or
3) a reduction in the amount of medicinal composition needed to achieve a therapeutic effect, for example less Premarin, resulting in lower cost to a patient and less risk.

ENDOMETRIUM

Prevention and treatment of endometrial abnormalities or disease.

Prevent endometrial hyperplasia/cancer caused by medications that stimulate the endometrium (e.g. tamoxifen).

In a particular embodiment of a method of the present invention for preventing and/or minimizing endometrial conditions, the method comprises having an individual ingest a pharmacological composition of the present invention wherein the pharmacological composition comprises a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

A preferred medicinal composition for this embodiment is a medicinal composition comprising tamoxifen, raloxifene or SERM's. The combination of a soy formulation of the present invention and a medicinal composition may provide one or more of the following advantages:

1) an additive benefit to heart and bone tissues while treating endometrial conditions;
2) reduced breast and endometrial proliferation, and prevention of endometrial hyperplasia/cancer (tamoxifen has been shown to promote formation of endometrial cancers, the soy formulation of the present invention may reduce this risk); or
3) a reduction in the amount of medicinal composition needed to achieve a therapeutic effect, for example less Premarin, resulting in lower cost to a patient and less risk.

HEAD/BRAIN SYMPTOMS

Prevention and treatment of Alzheimer's or other diseases of cognition.

Macular degeneration.

Migraine/vascular-related headaches.

Anxiety, nervousness, depression or other similar affective disorders

Hereditary hemorrhagic talengiectasia (HHT).

Male pattern baldness and female baldness.

Improvement in cognitive function.

In a particular embodiment of a method of the present invention for minimizing or alleviating head/brain symptoms, the method comprises having an individual ingest a pharmacological composition of the present invention wherein the pharmacological composition comprises a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

A preferred medicinal composition for this embodiment is a medicinal composition for Alzheimer's disease. The combination of a soy formulation of the present invention and a medicinal composition may provide one or more of the following advantages:

1) an additive benefit to heart and bone tissues while treating Alzheimer's symptoms;
2) a reduction in the amount of medicinal composition needed to achieve a therapeutic effect, resulting in lower cost to a patient and less risk.

GASTROINTESTINAL (GI) TRACT CONDITIONS

Any disorders of the gastrointestinal tract such as:

Constipation.

Peptic ulcers or other ulcers.

Gastroesophageal reflux (GERD).

Any inflammatory bowel diseases such as ulcerative colitis or Crohn's disease.

Cancers of the GI tract such as colon cancer.

SKIN/FACE CONDITIONS

Prevention of acne.

Treatment/reduction/prevention of facial wrinkling and sagging.

Prevention/treatment of skin cancers.

Growth stimulation of hair and nails.

Prevention/restoration of hair loss (men/women)

Promotion of strong nails and hair.

As understood by those of ordinary skill in the art, these skin/face conditions are often undesired side effects of a treatment protocol utilizing prescription drugs. Use of a pharmcological composition of the present invention comprising a soy formulation of the present invention and the prescription drug may advantageously reduce these conditions while also acheiving the desired therapeutic effect.

KIDNEY RELATED CONDITIONS

Prevention of disease, particularly diabetic nephropathies, polycystic kidney disease.

Improvement in kidney function such as increasing glomerular filtration rate (GFR).

Management of lipid abnormalities secondary to renal disease.

LUNG AND BREATHING RELATED CONDITIONS

Improvement in elasticity.

Treatment of cancers.

ADDITIONAL PROSTATE/URINARY TRACT CONDITIONS

Any prostate disorders.

Prevention/treatment of bladder or other reproductive tract cancers in men and women.

Prevention of death from prostate cancer (Japanese men have equal incidence of prostate cancer, but death rate is very low).

Treatment/prevention of symptoms of benign prostatic hyperplasia (BPH) (urgency, frequency, painful ejaculation, nocturia, etc.) and prostate cancer.

Prevention of prostrate cancer progression.

Treatment for impotence.

Lowering prostate specific antigen (PSA).

Lowering circulating dihydrotestosterone (DHT) levels.

Inhibition of 5-alpha reductase.

In a particular embodiment of a method of the present invention for acheiving these health benefits, the method comprises having an individual ingest a pharmacological composition of the present invention wherein the pharmacological composition comprises a soy formulation comprising 3 to 23 milligrams, preferably 5 to 15 milligrams, more preferably 6–9 milligrams of at least one isoflavone per gram of the formulation wherein the amount of the soy formulation is sufficient to provide greater than 60 milligrams, preferably greater than 200 milligrams, more preferably greater than 1800 milligrams, of at least one isoflavone per dose; and a medicinal composition wherein the amount of the medicinal composition is sufficient to achieve a desired therapeutic effect.

A preferred medicinal composition for this embodiment is a medicinal composition for estrogen replacement therapy or hormone replacement therapy (estrogen+progestins). Premarin is an example of a medicinal composition for this embodiment of the method of the present invention The combination of a soy formulation of the present invention and a medicinal composition for hormone replacement therapy and/or estrogen replacement therapy may provide one or more of the following advantages:

1) an additive benefit to heart and bone tissues while reducing menopausal symptoms;

2) reduction of estrogenic side effects (enlarged breasts, decreased libido, feminization)

3) reduced breast and endometrial proliferation; or 4) a reduction in the amount of medicinal composition needed to achieve a therapeutic effect, for example less Premarin, resulting in lower cost to a patient and less risk.

IMMUNE SYSTEM CONDITIONS

Autoimmune/rheumatological disorders such as sarcoidosis, rheumatoid arthritis, lupus.

Boosting immune system of immunocompromised individuals.

REPRODUCTIVE SYSTEM CONDITIONS

Increasing length of time between menstrual cycles.

Birth control at higher doses.

Increased fertility by causing regular menstrual cycles.

NERVOUS SYSTEM CONDITIONS

Treatment of pain, minimizing pain associated with trauma/surgery.

Treatment/minization of nerve damage associated with trauma/surgery.

It has been found that having mice ingest a soy formulation shortens time of neuropathies induced by nerve damage. Thus, for example, a breast cancer patient could take soy before surgery to minimize nerve damage/potential pain from surgery.

As understood by those of ordinary skill in the art, nervous system conditions/pain are often treated utilizing prescription drugs. Use of a pharmcological composition of the present invention comprising a soy formulation of the present invention and the prescription drug may advantageously provide the foregoing advantages thus reducing the amount of prescription drug necessary to acheive the desired therapeutic effect.

DIABETES ASSOCIATED DISEASES

Prevention of diabetic retinopathies.

Prevention/treatment of heart disease (see e.g. above).

Prevention/treatment of nerve damage (see e.g. above).

Prevention/treatment of kidney disease (see e.g. above).

EYE CONDITIONS

Prevention of cataracts and macular degeneration.

GENERAL CONDITIONS

Improvement in sexual function—men and women.

Obesity.

Treatment for chronic fatigue syndrome and fibromyalgia.

Treatment of hypo/hyperglycemia.

The following example illustrates the production of a soy formulation of the present invention which may be utilized in a dietary supplement and/or food product of the present invention and/or in a method of the present invention.

EXAMPLE

The following is one example of a blend of a first portion of higher isoflavone concentration soy product from the heart of the bean and a second portion of lower isoflavone concentration soy product to achieve a natural soy formulation of the present invention having an milligram isoflavone to gram soy protein ratio and a diadzin to genistin to glycitin ratio falling in the preferred ranges of the formulation of the present invention.

Soy product derived from the heart of the soybean produces relatively higher concentrations of isoflavones (24–36 mg of isoflavones per gram of protein). The higher isoflavone concentration soy product produced from the heart of the soy bean used in the present invention contains Diadzin/Diadzein: Genistin/Genistein: Glycitin/Glycitein in the average ratios of 3.33:1.00:2.33, respectively (Table 1). Soy derived from the whole soybean, such as found in soy product produced from the whole soy beans, yields relatively lower concentrations of isoflavones (<1.0–5 mg isoflavones per gram of protein). The lower isoflavone concentration soy product used in the present invention contains Diadzin/Diadzein: Genistin/Genistein: Glycitin/Glycitein in the average ratios of 5.00:10.00:1.00, respectively (Table 1). One example of the invention is a blend of approximately 4 grams of the higher isoflavone concentration soy product and approximately 18.4 grams of the lower isoflavone concentration soy product resulting in Diadzin/Diadzein: Genistin/Genistein: Glycitin/Glycitein in the approximate ratios of 2.00:1.00:1.00, respectively (Table 1).

TABLE 1

AVERAGE RATIOS OF ISOFLAVONES

| Isoflavone | Higher isoflavone concentration soy product (4 gm) | Lower isoflavone concentration soy product (18.4 gm) | Blend ratios (approximate) (22.4 gm) |
|---|---|---|---|
| Diadzin/Diadzein | 3.33 | 5.00 | 2.00 |
| Genistin/Genistein | 1.00 | 10.00 | 1.00 |
| Glycitin/Glycitein | 2.33 | 1.00 | 1.00 |

Long soybean crop histories and multiple testings of isoflavone concentrations in soy product derived therefrom consistently demonstrate these average ratios of constituent isoflavone concentrations in naturally grown soybeans. Naturally grown soybeans are defined as those without genetic modifications for isoflavone content. Actual ratios of constituent isoflavones in the final blended formulation depend on the relative amounts of higher isoflavone concentration soy product and lower isoflavone concentration soy product combined. The final soy formulation of the present invention preferably has an isoflavone concentration falling within the ranges discussed above. An example of a final soy composition of the present invention is illustrated in Table 2.

TABLE 2

| Isoflavone Concentration | grams Protein per gram formulation | mg Isoflavones per gram formulation | Total mg Isoflavones |
|---|---|---|---|
| Higher | 4 | 24–36 | 96–144 |
| Lower | 18.4 | <1.0–3.4 | <18.4–62.56 |
| Total | 22.4 | 6–9 | <114.4–206.56 |

Although the invention has been described with reference to particular embodiments and features, other similar embodiments and features may be utilized to obtain similar results. Variations and modifications of the soy formulations, dietary supplements, food products and methods of the present invention will be apparent to one skilled in the art and the present disclosure is intended to cover all such modifications and equivalents within the scope of the following claims.

What is claimed is:

1. A soy formulation comprising:
    a first produced from the heart of a soybean; and
    a second portion produced from a whole soy bean;
    wherein the soy formulation comprises 3 to 23 milligrams of a plurality of isoflavones comprising diadzin, genistin and glycitin per gram of the formulation wherein, the diadzin to genistin to glycitin ratio is between 3:1:2 and 3:4.5:1.

2. The soy formulation of claim 1 wherein the soy formulation comprises 5 to 15 milligrams of at least one isoflavones per gram of the formulation.

3. The soy formulation of claim 2 wherein the soy formulation comprises 6 to 9 milligrams of at least one isoflavones per gram of the formulation.

4. The soy formulation of claim 1 wherein the soy formulation further comprises 0.4 to 1.2 grams protein per gram of the formulation.

5. The natural soy formulation of claim 4 wherein the soy formulation comprises 6 to 9 milligrams of at least one of the isoflavones per gram of the formulation.

6. The soy formulation of claim 5 wherein the soy formulation comprises 0.4 to 0.9 grams protein per gram of the formulation.

7. A dietary supplement comprising:
    40 to 90%, by weight, protein;
    1 to 59%, by weight, carbohydrate; and
    1 to 10%, by weight, fat;
    wherein the protein comprises the soy formulation of claim 1 wherein the amount of the soy formulation in the dietary supplement is sufficient to provide greater than 60 milligrams of at least one isoflavone per serving.

8. A food product comprising:
    20 to 40%, by weight, protein;
    10 to 80%, by weight, carbohydrate; and
    1 to 10%, by weight, fat;
    wherein the protein comprises the soy formulation of claim 1 wherein the amount of the soy formulation in the food product is sufficient to provide greater than 60 milligrams of at least one isoflavone per serving.

9. The food product of claim 1 further comprising one or more of the following components: preservatives, flavorings, vitamins, and/or minerals.

10. The food product of claim 8 wherein the food product comprises:
    30 to 32%, by weight the soy formulation of claim 1;
    55 to 57%, by weight carbohydrate;
    3 to 5%, by weight fat;
    0.2 to 1%, by weight calcium;
    0.2 to 1%, by weight phosphorous;
    0.1 to 0.7%, by weight sodium;
    0.2 to 1%, by weight potassium; and
    2.3 to 11.3%, by weight of one or more of the following components: cocoa, calcium phosphate, maltodextrin, soy lecithin, salt, potassium chloride, artificial flavor, carrageenan, carboxymethyl cellulose and/or xanthan gum.

11. A pharmcological composition comprising a biologically compatible inert carrier and the soy formulation of claim 1 wherein the amount of the so formulation in the pharmacological composition is sufficient to provide greater than 60 milligrams of at least one isoflavone per dose.

12. The pharmacological composition of claim 11 further comprising a medicinal composition.

13. A soy formulation comprising:
a first portion produced from the heart of a soybean; and
a second portion produced from a whole soy bean;
wherein the soy formulation comprises
3 to 23 milligrams of a plurality of isoflavones comprising diadzin, genistin and glycitin per gram; and
0.4 to 1.2 grams protein;
per gram of the formulation;
wherein the diadzin to genistin to glycitin ratio is between 3:1:2 and 3:4.5:1.

14. The soy formulation of claim 13 wherein the soy formulation comprises 5 to 15 milligrams of at least one of the isoflavones per gram of the formulation.

15. The soy formulation of claim 14 wherein the soy formulation comprises 6 to 9 milligrams of at least one of the isoflavones per gram of the formulation.

16. The soy formulation of claim 15 wherein the soy formulation comprises 0.4 to 0.9 grams protein per gram of the formulation.

17. The soy formulation of claim 13 wherein the soy formulation comprises 0.4 to 0.9 grams protein per gram of the formulation.

18. A dietary supplement comprising:
40 to 90%, by weight, protein;
1 to 59%, by weight, carbohydrate; and
1 to 10%, by weight, fat;
wherein the protein comprises the soy formulation of claim 13 wherein the amount of the soy formulation in the dietary supplement is sufficient to provide greater than 60 milligrams of at least one isoflavone per serving.

19. A food product comprising:
20 to 40%, by weight, protein;
10 to 80%, by weight, carbohydrate; and
1 to 10%, by weight, fat;
wherein the protein comprises the soy formulation of claim 13 wherein the amount of the soy formulation in the food product is sufficient to provide greater than 60 milligrams of at least one isoflavone per serving.

20. The food product of claim 19 further comprising one or more of the following components: preservatives, flavorings, vitamins, and/or minerals.

21. The food product of claim 19 wherein the food product comprises:
30 to 32%, by weight the soy formulation of claim 13;
55 to 57%, by weight carbohydrate;
3 to 5%, by weight fat;
0.2 to 1%, by weight calcium;
0.2 to 1%, by weight phosphorous;
0.1 to 0.7%, by weight sodium;
0.2 to 1%, by weight potassium; and
2.3 to 11.3%, by weight of one or more of the following components: cocoa, calcium phosphate, maltodextrin, soy lecithin, salt, potassium chloride, artificial flavor, carrageenan, carboxymethyl cellulose and/or xanthan gum.

22. A pharmacological composition comprising a biologically compatible inert carrier and the soy formulation of claim 13 wherein the amount of the soy formulation in the pharmacological composition is sufficient to provide greater than 60 milligrams of at least one isoflavone per dose.

23. The pharmacological composition of claim 22 further comprising a medicinal composition.

* * * * *

UNITED STATES PATENT AND TRADEMARK OFFICE
CERTIFICATE OF CORRECTION

PATENT NO.     : 6,482,448 B2
DATED          : November 19, 2002
INVENTOR(S)    : Tabor, Aaron It is certified that error appears in the above-identified patent and that said Letters Patent is hereby corrected as shown below:

Column 20,
Line 3, "a first produced" should read -- a first portion produced --.
Line 43, "food product of claim 1" should read -- food product of claim 8 --.
Line 63, "amount of the so formulation" should read -- amount of the soy formulation --.

Signed and Sealed this

Eighth Day of April, 2003

JAMES E. ROGAN
*Director of the United States Patent and Trademark Office*